United States Patent [19]

Gall

[11] Patent Number: 5,289,438

[45] Date of Patent: Feb. 22, 1994

[54] METHOD AND SYSTEM FOR ALTERING CONSCIOUSNESS

[76] Inventor: James Gall, 16621 E. Jacklin Dr., Fountain Hills, Ariz. 85268

[21] Appl. No.: 867,326

[22] Filed: Apr. 13, 1992

Related U.S. Application Data

[62] Division of Ser. No. 642,439, Jan. 17, 1991, Pat. No. 5,123,899.

[51] Int. Cl.$^5$ ............................................. G10F 1/00
[52] U.S. Cl. .................................... 369/4; 600/28; 128/905
[58] Field of Search ................ 369/4, 127, 15; 360/5, 360/1; 600/28, 26; 128/905

[56] References Cited

U.S. PATENT DOCUMENTS

| | | | |
|---|---|---|---|
| 4,141,344 | 2/1979 | Barbara | 600/28 |
| 4,315,502 | 2/1982 | Gorges | 600/27 |
| 4,503,863 | 3/1985 | Katims | 600/26 |
| 4,883,067 | 11/1989 | Knispel et al. | 600/28 |
| 5,123,899 | 6/1993 | Gall | 600/28 |

Primary Examiner—Robert J. Pascal
Assistant Examiner—Tan Dinh
Attorney, Agent, or Firm—Cahill, Sutton & Thomas

[57] ABSTRACT

A system for altering the states of human consciousness involves the simultaneous application of multiple stimuli, preferable sounds, having differing frequencies and wave forms. The relationship between the frequencies of the several stimuli is exhibited by the equation $$g = 2^{n/4} \cdot f$$

where:
 f = frequency of one stimulus;
 g = frequency of the other stimuli or stimulus; and
 n = a positive or negative integer which is different for each other stimulus.

2 Claims, 1 Drawing Sheet

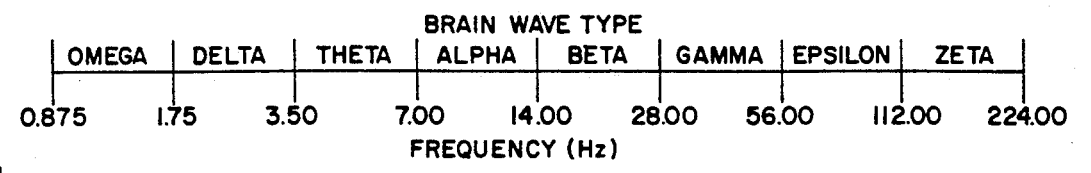
*FIG. 1*
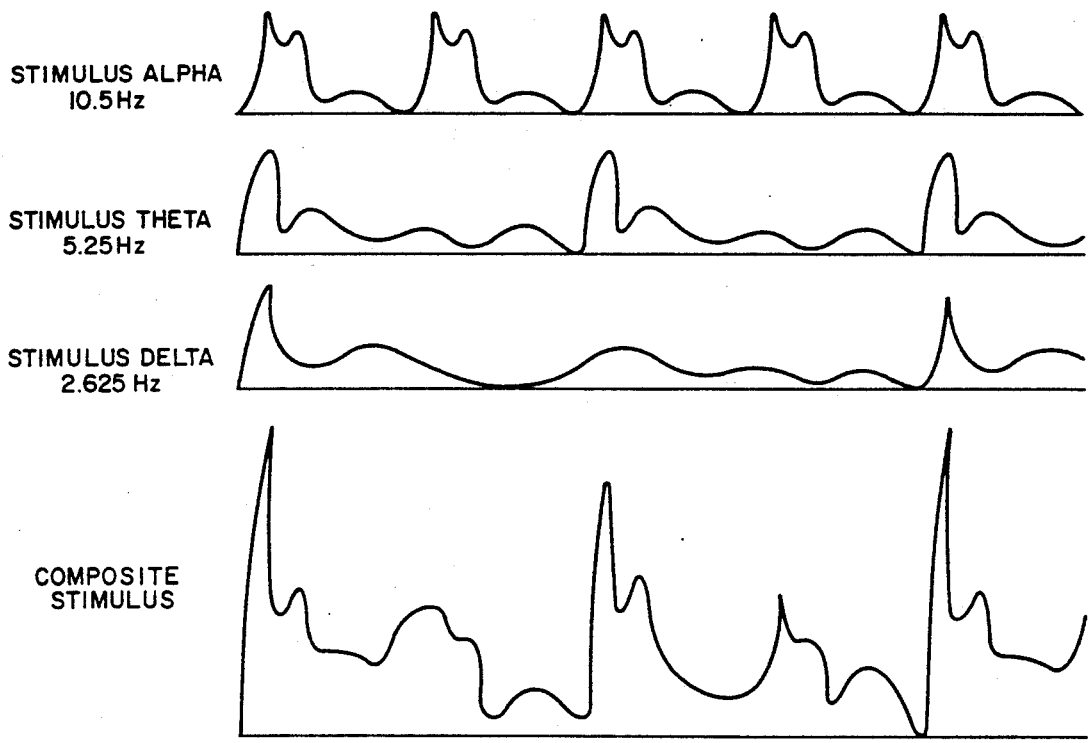
*FIG. 2*
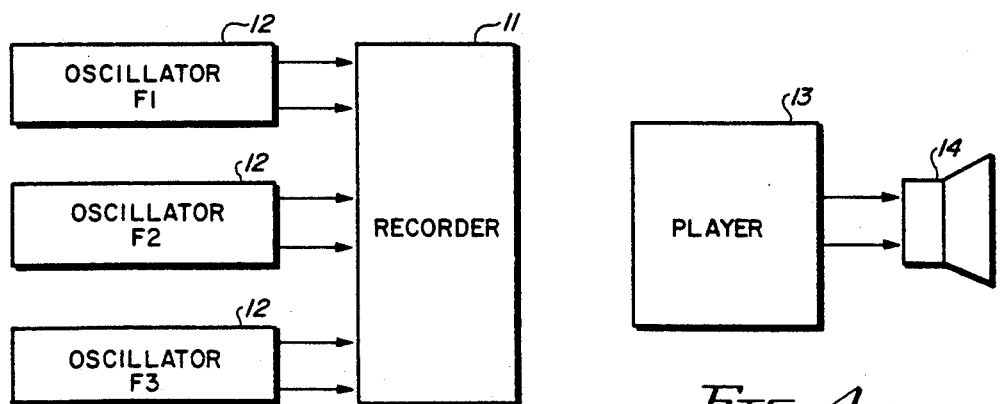
*FIG. 3*
*FIG. 4*

METHOD AND SYSTEM FOR ALTERING CONSCIOUSNESS

This application is a division of application Ser. No. 07/642,439, filed Jan. 17, 1991 as now is U.S.A. 5,123,899.

TECHNICAL FIELD

This invention is concerned with the application of stimuli to a human subject to induce different states of consciousness.

BACKGROUND ART

It is well accepted in scientific circles that there is a correlation between the electroencephalographic wave rhythms exhibited by the brain of a human and the state of consciousness of that being. Rhythms customarily found in the normal human adult when he is relaxed and his eyes closed have a pulse frequency in the seven-fourteen Hz. range and have come to be identified as "alpha" rhythms. Similarly, when a person is aroused and anxious, the rhythms exhibited fall in the 14–28 Hz. range and are known as "beta" rhythms. A normal person in sleep exhibits "delta" rhythms in the 1.75–3.5 Hz. range. Other brain wave rhythms which have been identified by researchers as being associated with various normal and abnormal states of consciousness are: "theta", 3.5–7.0 Hz. and "gamma", 28–56 Hz. Research by the applicant has led to the identification and naming of three additional rhythms, namely: "omega", 0.875–1.75 Hz.; "epsilon", 56–112 Hz.; and "zeta", 112–224 Hz.

Researchers have devised a variety of systems for stimulating the brain to exhibit specific brain wave rhythms and thereby alter the state of consciousness of the individual subject. Most of these efforts have been aimed at inducing an alpha, or relaxed, brain wave rhythm or a delta, or sleep, brain wave rhythm.

E. W. Ballentine and B. C. Gindes, in their U.S. Pat. No. 3,762,396, granted Oct. 2, 1973, for "Method and Apparatus for Inducing Sleep by Applying Electrical Pulses to Plural Portions of the Head", disclose a system for inducing sleep, treating psychosomatic disorders, and aiding the induction of hypnosis. With this system, the patient is subjected to three stimuli. The first stimulus is electrical current pulses having a frequency of 8–10 CPS applied by electrodes to the back of the head. A second stimulus of electrical current pulses having a frequency four times the frequency of the first stimulus is applied to the optic nerve through electrodes on the forehead. The third stimulus is a sound signal produced by the first stimulus and applied to the patient via sound attenuating chambers in order to isolate the patient from a noisy environment.

U.S. Pat. No. 3,576,185 was granted Apr. 27, 1971, to H. Shulz for "Sleep-Inducing Method and Arrangement Using Modulated Sound and Light". This patent describes an apparatus and a method for inducing sleep by directing at the subject two sound signals in the range of 40–80 Hz., free of overtones and amplitude modulated between the perceivable minimum and a perceivable maximum. The two signals differ in frequency by approximately 0.5–2 Hz. Optical stimuli may also be used.

K. Masaki in his U.S. Pat. No. 4,834,701, granted May 30, 1989, for "Apparatus for Inducing Frequency Reduction in Brain Wave" states his objective to be the reduction of beta-rhythm into alpha-rhythm as well as to retain alpha-rhythm. The subject is subjected to two sound signals which are each higher in frequency than 4–16 Hz. But are different and produce a beat signal which is within the 4–16 Hz. range. It is represented that the subject exhibits improve ability in learning, researching and inventing.

B. C. Gindes also teamed with B. C. Meland to obtain U.S. Pat. No. 4,227,516, granted Oct. 14, 1980, for "Apparatus for Electrophysiological Stimulation". This patent discloses apparatus for stimulating the effects of brain wave activity in one of the delta, theta, alpha, and beta brain wave frequency ranges. A first wave is generated in a frequency range above the brain wave ranges. This first wave is then modulated by a second wave having a frequency within one of the brain wave frequencies. The modulated first waves are applied to the subject by means of electrodes on the forehead. The second wave may also be applied by sound through headphones. A third wave in a range 150–600 Hz. may be modulated by the second wave and the modulated tone that is produced applied to headphones worn by the subject. The system is represented as being able to, among other things, induce sleep, induce a hypnotic state, produce heightened awareness and increase the ability of a person to concentrate.

Each of the systems disclosed in these prior patents require that fairly complex apparatus be directly associated with the subject. And the systems of the two Gindes, et.al. patents hamper useful activity of the subject by the requirement that the subject be attached to electrodes and earphones.

There continues to be a need for a system for inducing brain wave rhythms which is inexpensive and easy to use from the subject's point of view.

DISCLOSURE OF THE INVENTION

This invention contemplates utilizing a plurality of brain wave rhythm stimuli simultaneously with each stimulus having a specific frequency relationship with every other stimulus. That relationship is expressed in the following equation:

$$g = 2^{n/4} \cdot f$$

when f is the frequency of one stimulus, g is the corresponding frequency for each of the other stimulus or stimuli and n is a positive or negative integer. Although visual and electrical current stimuli can be employed in the system of this invention, aural stimuli are preferred. The latter can be recorded on small, convenient tape or disc records and played back by the subject on an inexpensive portable player.

BRIEF DESCRIPTION OF THE DRAWINGS

The invention is described in greater detail hereinafter by reference to the accompanying drawings, wherein:

FIG. 1 is a graphic presentation of the various types of brain wave rhythms with which this invention is concerned;

FIG. 2 illustrates graphically how a plurality of brain wave stimuli are combined to produce a brain wave rhythm according to the invention;

FIG. 3 is a block diagram of brain wave rhythm stimuli recording apparatus employed in the invention; and FIG. 4 is a block diagram of brain wave rhythm stimuli playback apparatus employed in the invention.

BEST MODE FOR CARRYING OUT THE INVENTION

Referring particularly to FIG. 1, depicted there are the several types, or ranges, of brain wave rhythms for which stimuli can be selected and utilized in accordance with this invention. It has been recognized that the human brain tends to imitate or endeavor to duplicate the rhythm it is subjected to via outside stimuli. For example, if the subject is subjected to sound producing a beat in the range of 4-16 Hz. as proposed by the Masaki patent identified above, the subject's brain is influenced to exhibit a similar electroencephalographic wave rhythm giving the subject an alpha state of consciousness.

Research has demonstrated that the subject need not be conscious of, i.e. need not actually hear, an aural stimulus in order for the brain to detect and seek to emulate and synchronize with that stimulus.

The discovery at the heart of the present invention is that a greater range of altered consciousness can be achieved through the simultaneous application of multiple stimuli possessing specific harmonic relationships. In accordance with this invention, that relationship can be expressed as:

$$g = 2^{n/4} \cdot f$$

where:
 f = frequency of one stimulus;
 g = frequency of each other stimulus or stimuli; and
 n = a plus or minus integer which is different for each other stimulus.

By way of example, if one stimulus, f, has a frequency of 10 Hz., the frequencies, g, for the other stimuli must be selected from among the following (all expressed in Hz.):

| n  | g     | n  | g      |
|----|-------|----|--------|
| -8 | 2.5   | +1 | 11.892 |
| -7 | 2.973 | +2 | 14.142 |
| -6 | 3.536 | +3 | 16.818 |
| -5 | 4.204 | +4 | 20     |
| -4 | 5     | +5 | 23.784 |
| -3 | 5.946 | +6 | 28.284 |
| -2 | 7.071 | +7 | 33.636 |
| -1 | 8.409 | +8 | 40     |

From this table, it can be observed that the frequencies of the several stimuli bear another relationship. And that relationship is that within an octave (a range in which the frequency is doubled) there are but three intermediate equally spaced frequencies. Stated somewhat differently, the frequencies of two adjacent stimuli are spaced no more closely than one-quarter of an octave.

Another desired characteristic of the multiple stimuli brain wave rhythm of this invention is that each stimulus exhibit a discrete wave pattern different from the wave pattern of the other stimuli or stimulus. FIG. 2 illustrates how three different aural stimuli are combined to produce a sound from which the individual stimulus can be perceived and distinguished by the subject's brain. This characteristic is believed to be important in producing effective brain wave rhythms.

On the other hand, research has revealed that effective brain wave rhythm inducement can be carried out regardless of the phase relationship between the several stimuli. The stimuli frequencies need not be synchronized.

As mentioned previously, the application of multiple stimuli in accordance with this invention induces brain wave rhythms offering a greater range of altered consciousness than is achievable with prior systems. Improved results can be obtained using only two or three stimuli, but more complex states of consciousness can be induced utilizing as many as seven stimuli spread across the entire range of brain wave rhythm types illustrated in FIG. 1.

The simpler, two and three stimuli, brain wave rhythms of this invention can be employed to improve sleep patterns, increase dream recall activity, reduce stress, and enhance the subject's sense of well-being and contentment. The more complex, multi-stimuli rhythms are more effective than the simpler rhythms and are useful in inducing levels of consciousness wherein the ability to work fast and perform complex tasks@is enhanced. These multi-stimuli rhythms are also useful in the reduction of emotional distress associated with long-forgotten, traumatic events in the subject's life.

FIGS. 3 and 4 illustrate the simple apparatus required to practice this invention. Records of the brain wave stimuli are produced in a recorder 11 to which a plurality of oscillators 12 provide the selected frequencies and wave forms for the individual stimuli. The records thus produced can be played by a subject on a record player 13 having a speaker 14. The frequencies employed here, namely in the range of about 0.1 Hz. to 200 Hz., can be reproduced by inexpensive record playing equipment. No high-fidelity player is required.

This description of the invention has emphasized the use of aural stimuli, but, as mentioned previously, the stimuli may take the form of light energies for visual stimulation or eletrical current for direct tactile stimulations.

What is claimed is:

1. A method of making a sound recording comprising the steps of producing and recording a first sound having a uniform frequency and a distinctive wave form, and simultaneously producing and recording on the same record a second sound having a different wave form and having a frequency which is related to the frequency of the first sound by the equation:

$$g = 2^{n/4} \cdot f$$

wherein:
 f = the frequency of the first sound;
 g = the frequency of the second sound; and
 n = a positive or negative integer.

2. The recording produced by the method of claim 1.

* * * * *